US009194012B2

(12) United States Patent
Hamrick

(10) Patent No.: US 9,194,012 B2
(45) Date of Patent: Nov. 24, 2015

(54) METHODS AND SYSTEMS FOR PRODUCING SUGARS FROM CARBOHYDRATE-RICH SUBSTRATES

(71) Applicant: Edward Brian Hamrick, Sunny Isles Beach, FL (US)

(72) Inventor: Edward Brian Hamrick, Sunny Isles Beach, FL (US)

(*) Notice: Subject to any disclaimer, the term of this patent is extended or adjusted under 35 U.S.C. 154(b) by 0 days.

(21) Appl. No.: 14/608,183

(22) Filed: Jan. 28, 2015

(65) Prior Publication Data

US 2015/0218663 A1 Aug. 6, 2015

Related U.S. Application Data

(60) Provisional application No. 61/934,799, filed on Feb. 2, 2014.

(51) Int. Cl.
| | |
|---|---|
| *C13K 1/02* | (2006.01) |
| *C13K 13/00* | (2006.01) |
| *C12P 19/00* | (2006.01) |
| *C08H 8/00* | (2010.01) |
| *C12P 19/14* | (2006.01) |
| *C12P 19/02* | (2006.01) |

(52) U.S. Cl.
CPC .. *C13K 1/02* (2013.01); *C08H 8/00* (2013.01); *C12P 19/00* (2013.01); *C12P 19/02* (2013.01); *C12P 19/14* (2013.01); *C13K 13/00* (2013.01); *C13K 13/002* (2013.01)

(58) Field of Classification Search
None
See application file for complete search history.

(56) References Cited

U.S. PATENT DOCUMENTS

| 3,212,932 A | 10/1965 | Hess et al. |
|---|---|---|
| 5,411,594 A | 5/1995 | Brelsford |
| 7,700,764 B2 | 4/2010 | Heijnesson-Hultén |
| 8,298,796 B2 | 10/2012 | Tolan et al. |
| 2002/0192774 A1* | 12/2002 | Ahring et al. ............. 435/162 |

(Continued)

FOREIGN PATENT DOCUMENTS

| CA | 2872456 | 5/2013 |
|---|---|---|
| EP | 0044658 B2 | 9/1992 |

(Continued)

OTHER PUBLICATIONS

Nelson, "Apparent Activation Energy of Hydrolysis of Some Cellulosic Materials," Journal of Polymer Science vol. XLIII, pp. 351-371 (1960).

(Continued)

*Primary Examiner* — Melvin C Mayes
*Assistant Examiner* — Douglas Call
(74) *Attorney, Agent, or Firm* — O'Connor & Company; Ryan P. O'Connor

(57) ABSTRACT

A method for producing sugars from lignocellulosic biomass is provided. Lignocellulosic biomass is composed of lignocellulosic fibers which are hollow and primarily contain cellulose, hemicellulose and lignin. Lignin is concentrated in the outer fiber wall and glues the fibers into bundles, but the inner fiber wall has a much lower concentration of lignin and has more easily accessible cellulose and hemicellulose. This method uses vacuum infusion to infuse homogeneous reagents into the lumen (hollow center) of lignocellulosic fibers to hydrolyze the hemicellulose and cellulose to produce sugars and oligomers, and then uses cycles of vacuum pressure to pump these homogeneous reagents and sugars and oligomers into and out of the lumen. Some types of reagents are dilute acids, cellulase enzymes, hemicellulase enzymes, Fenton or Fenton-like reagents, and hydrogen peroxide. These reagents are homogenized by mixing the reagents with process water using turbulent mixing to produce a homogeneous reagent.

25 Claims, 1 Drawing Sheet

(56) References Cited

U.S. PATENT DOCUMENTS

| | | | |
|---|---|---|---|
| 2003/0173291 | A1 | 9/2003 | Schimel |
| 2006/0124124 | A1* | 6/2006 | Soni et al. ............... 127/37 |
| 2006/0289132 | A1 | 12/2006 | Heijnesson-Hulten |
| 2007/0031918 | A1* | 2/2007 | Dunson et al. ............ 435/41 |
| 2009/0050134 | A1* | 2/2009 | Friend et al. ............. 127/29 |
| 2009/0053770 | A1* | 2/2009 | Hennessey et al. ........ 435/72 |
| 2009/0093028 | A1 | 4/2009 | Peterson |
| 2009/0098618 | A1 | 4/2009 | Burke et al. |
| 2010/0270499 | A1 | 10/2010 | Fang et al. |
| 2011/0100359 | A1* | 5/2011 | North ....................... 127/1 |
| 2012/0122162 | A1* | 5/2012 | Romero et al. ........... 435/99 |
| 2013/0152457 | A1 | 6/2013 | Powell et al. |
| 2013/0274456 | A1* | 10/2013 | Parekh et al. ........... 536/1.11 |
| 2013/0295629 | A1 | 11/2013 | Weider et al. |
| 2014/0200335 | A1 | 7/2014 | Olkowski et al. |
| 2014/0315258 | A1* | 10/2014 | Nguyen .................... 435/99 |

FOREIGN PATENT DOCUMENTS

| | | |
|---|---|---|
| WO | 0132715 A1 | 5/2001 |
| WO | 2004081185 A2 | 9/2004 |
| WO | 2006024242 A1 | 3/2006 |
| WO | 2012155239 A1 | 11/2012 |
| WO | 2013025564 A2 | 2/2013 |
| WO | 2013092881 A2 | 6/2013 |

OTHER PUBLICATIONS

Xu et al., Kinetics of Acid Hydrolysis of Water-Soluble Spruce O-Acetyl Galactoglucomannans, J. Agric. Food Chem. 2008, 56, 2429-2435.

Khamaruddin et al., "Using Fenton's Reagents for the Degradation of Diisopropanolamine: Effect of Temperature and pH," 2011 International Conference on Environment and Industrial Innovation IPCBEE vol. 12 (2011).

Lenihan et al., "Kinetic modelling of dilute acid hydrolysis of lignocellulosic biomass," Biofuel production—recent developments and prospects, InTech, Croatia (2011): 293-308.

Peng et al., "Chemistry and Applications of Nanocrystalline Cellulose and its Derivatives: a Nanotechnology Perspective," The Canadian Journal of Chemical Engineering, vol. 9999, 2011.

Gibson, "The hierarchical structure and mechanics of plant materials," J. R. Soc. Interface published online Aug. 8, 2012.

Gierlinger et al., "Raman Imaging of Lignocellulosic Feedstock," Chapter 8 in Cellulose—Biomass Conversion (2013).

Lan et al., "Enzymatic Saccharification of Lignocelluloses Should be Conducted at Elevated pH 5.2-6.2," Bioenerg. Res. (2013) 6:476-485.

de Tuesta et al., "Application of high-temperature Fenton oxidation for the treatment of sulfonation plant wastewater," J Chem Technol Biotechnol (2014).

Gierlinger, "Revealing changes in molecular composition of plant cell walls on the micron-level by Raman mapping and vertex component analysis (VCA)," Jun. 2014 | vol. 5 | Article 306.

Azhar et al., "Extraction of hemicelluloses from fiberized spruce wood," Carbohydrate Polymers 117 (2015) 19-24.

US Department of Energy, National Renewable Energy Laboratory Technical Report NREL/TP-510-42628 issued on Jan. 2008.

* cited by examiner

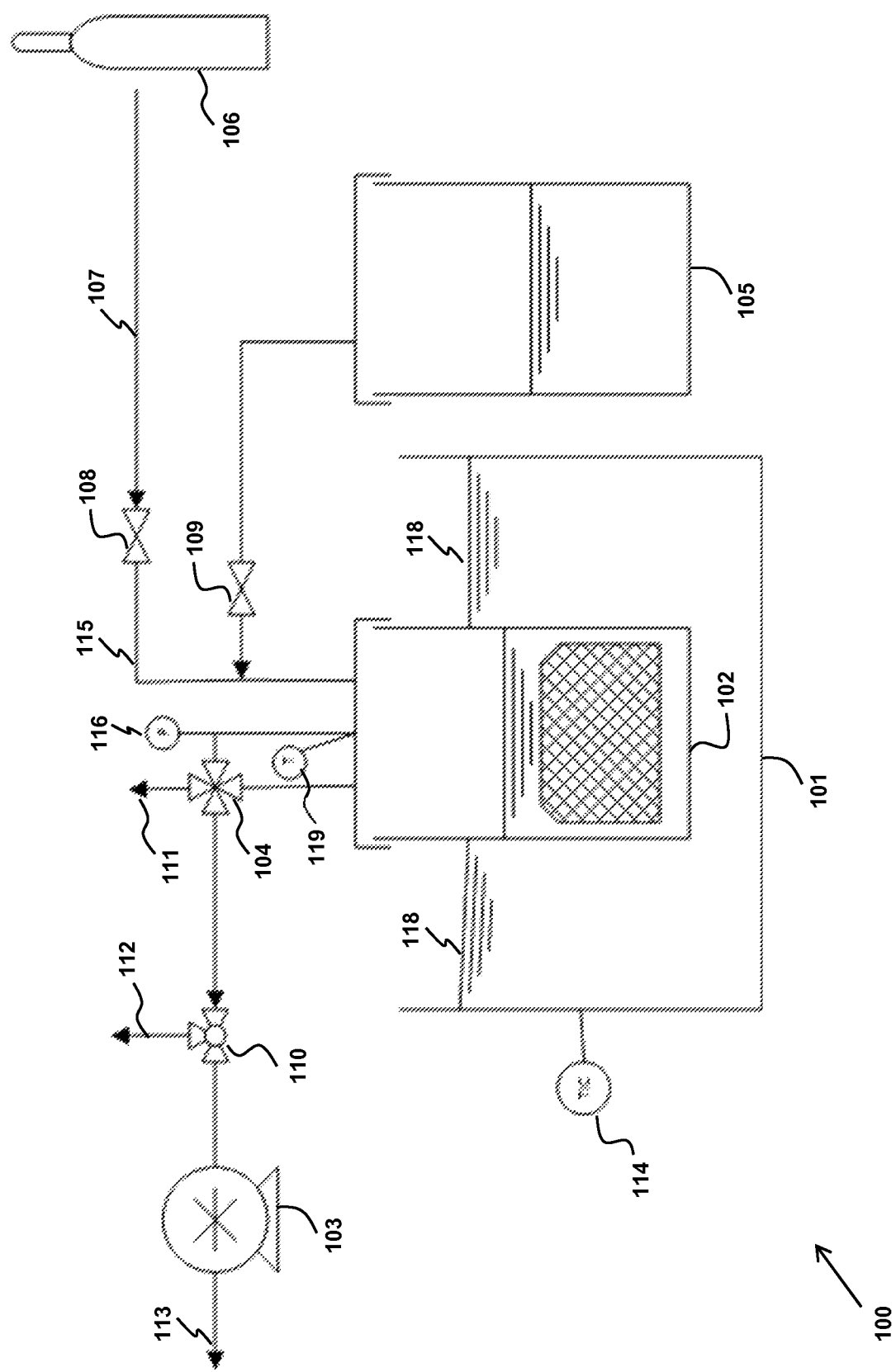

US 9,194,012 B2

METHODS AND SYSTEMS FOR PRODUCING SUGARS FROM CARBOHYDRATE-RICH SUBSTRATES

PRIORITY DATA

This patent application is a non-provisional application with priority to U.S. Provisional Patent App. No. 61/934,799, filed Feb. 2, 2014, which is hereby incorporated by reference herein.

FIELD OF THE INVENTION

The present invention generally relates to methods for saccharification of lignocellulosic biomass and related substrates.

BACKGROUND OF THE INVENTION

Carbohydrate-rich materials such as naturally occurring lignocellulosic biomass (wood, agricultural residues, etc.) or manmade products such as size-reduced softwood, paper, cardboard, and so on are an important source of non-food simple sugars, oligomers, and polymers for a variety of industrial applications. These materials consist primarily of ligno-cellulosic fibers which are typically comprised of cellulose, hemicellulose, and lignin. Cellulose is a polymer of glucose, hemicellulose is a polymer of a variety of hexose and pentose sugars (primarily mannose in softwood and xylose in other biomass), and lignin is an aromatic polymer. The main hexose sugars in biomass are glucose, mannose and galactose, and the main pentose sugars in biomass are xylose and arabinose. The relative amount of cellulose, hemicellulose and lignin of various materials is highly dependent on the specific type of biomass.

Regardless of its type, biomass is composed of fibers "glued" into bundles. The glue is primarily lignin, and is concentrated in the compound middle lamella (the outer layer of fibers). Much of the cost of extracting sugars from biomass using existing methods is in separating fibers and removing (or relocating) the lignin on the outside of the fibers so that the cellulose and hemicellulose in the fibers are more easily accessible from the outside of the fibers. For instance, making paper pulp (separated fibers) from wood chips is very energy-intensive, requiring rather extreme operating conditions and in the case of Kraft or sulfite pulp, also harsh chemicals. Similarly, the energy required to separate fibers using steam explosion, ammonia fiber expansion, or other pretreatment techniques make it cost prohibitive to process biomass into separate fibers amenable for sugar extraction.

Fibers are hollow, usually filled with air, typically with a roughly round profile. The hollow part of a fiber is called the lumen, and is typically about 36% of the volume of a fiber. The density of the cell wall is roughly 1.5 g/cm$^3$, and the overall density of most fibers (when the air-filled center is taken into account) is roughly 0.96 g/cm$^3$. For this reason, most dry or partially moist biomass particles generally float in water. The air pockets in biomass are not easily displaced with water, which is why wood or straw bales will float for weeks or months before sinking.

Fibers generally are between 1 and 4 mm long and about 20 to 40 microns in diameter, depending on the type of plant that produced them. The walls of these fibers contain a large number of holes, called pits or pores, ranging in size from 30 nm to 1000 nm. The cell wall is about 20% of the diameter of a fiber, resulting in the lumen having about 36% of the volume of a typical fiber. The characteristics of biomass are described in more detail in Gibson, "The hierarchical structure and mechanics of plant materials," *Journal of The Royal Society Interface* 9 76 (2012): 2749-2766, which is hereby incorporated by reference herein.

The inner surface of the cell wall of fibers, starting at the lumen, has the lowest concentration of lignin in fibers. The distribution of cellulose, hemicellulose, and lignin in plant cell walls is described in detail by Gierlinger et al., "Raman Imaging of Lignocellulosic Feedstock," in *Cellulose—Biomass Conversion*, edited by van de Ven and Kadla (2013): 159, and in Gierlinger, "Revealing changes in molecular composition of plant cell walls on the micron-level by Raman mapping and vertex component analysis (VCA)," *Frontiers in plant science* 5 (2014), both of which are hereby incorporated by reference herein.

The degree of polymerization (DP) is defined as the number of monomeric units in a macromolecule. In the case of cellulose and hemicellulose, the monomeric units are simple sugars. In biomass, reducing the degree of polymerization of cellulose and hemicellulose can be done with reagents that cause hydrolysis and/or oxidation reactions. The cellulose and hemicellulose contained in fibers can be hydrolyzed to hexose monomeric sugars such as glucose and mannose and to pentose monomeric sugars such as xylose and arabinose. Cellulase enzymes, hemicellulase enzymes, dilute acid solutions, strong acids, and strong bases catalyze these hydrolysis reactions. Hydrolysis also can be carried out at high temperatures in the absence of a catalyst. The degree of polymerization of cellulose and hemicellulose can also be reduced by oxidation with a Fenton or Fenton-like reagent, composed of a transition metal catalyst in solution with hydrogen peroxide Sugars have significant economic value and can be fermented to liquid fuels such as ethanol, butanol, or other specialty chemicals and can also be used for animal nutrition. Polymeric sugars, such as nanocellulose crystals, have increasingly considerable industrial interest and economic value because of possible application in the development of novel high performance renewable materials. Lignin and sugar monomers are not significantly degraded at 90° C. at a pH of 1.0 and above, but oligomers and polymers of cellulose and hemicellulose are randomly hydrolyzed. Amorphous regions of cellulose are quickly hydrolyzed at a pH less than 2 and a temperature of about 90° C., as is hemicellulose (which is also amorphous). Crystalline regions of cellulose fibrils are not significantly degraded at a pH above 1.0 and 90° C. because of the hydrogen bonds between cellulose chains in crystalline cellulose.

When hydrolyzing biomass to produce sugars, one of the fundamental limitations involved is mass transfer of sugars out of the bulk fibers, due to limitations of simple diffusion. A solution is desired. What is especially needed in the biorefining industry is a method to reduce the cost of extracting sugars from biomass by eliminating the costly step of separating the fibers and relocating the lignin on the outside of the fibers. It is also highly desirable to reduce the high capital and operating costs associated with biomass size reduction and mechanical mixing during hydrolysis.

SUMMARY OF THE INVENTION

In some variations, the invention provides a process for producing sugar monomers and/or polymers from a carbohydrate-rich substrate, the process comprising the steps of:

(a) providing a reaction mixture comprising a carbohydrate-rich substrate and a liquid solution containing a hydrolysis catalyst;

(b) exposing the reaction mixture to a gas-phase reaction pressure;

(c) maintaining the reaction mixture at a reaction temperature for a reaction time to generate the sugar monomers and/or polymers within lumen space of the carbohydrate-rich substrate;

(d) exposing the reaction mixture to a gas-phase expulsion pressure that is lower than the reaction pressure, to expel the sugar monomers and/or polymers out of the lumen space and into the liquid solution;

(e) maintaining the reaction mixture at an expulsion temperature for an expulsion time;

(f) repeating steps (b) to (e) for a number of pressure cycles; and (g) recovering the sugar monomers and/or polymers.

In some embodiments, the carbohydrate-rich substrate is selected from the group consisting of naturally occurring lignocellulosic biomass, processed lignocellulosic biomass, pulp, paper, paper-based products, carbohydrate-rich industrial waste, and combinations thereof. In certain embodiments, the carbohydrate-rich substrate includes naturally occurring lignocellulosic biomass selected from the group consisting of size-reduced softwood, sugarcane bagasse, wheat straw, corn stover, switchgrass, miscanthus, and combinations thereof. In some embodiments, the carbohydrate-rich substrate includes carbohydrate-rich industrial waste selected from the group consisting of food waste, components of municipal solid waste, and combinations thereof.

The sugar monomers and/or polymers may include hexose sugars in monomer, oligomer, or polymer form, including one or more of glucose, mannose, galactose, O-acetyl galactoglucomannan, and nanocellulose crystals. The sugar monomers and/or polymers may also include pentose sugars in monomer, oligomer, or polymer form, including xylose and/or arabinose.

In some embodiments, the hydrolysis catalyst comprises an organic acid, a mineral acid, hydrogen peroxide, or a combination thereof. For example, the hydrolysis catalyst may comprise sulfuric acid in an amount that results in the liquid solution having a sulfuric acid concentration of about 10 mM to about 200 mM.

In these or other embodiments, the hydrolysis catalyst may comprise one or more Fenton or Fenton-like reagents including hydrogen peroxide and one or multiple transition metals, such as a metal selected from iron, manganese, or combinations thereof. In some embodiments, the hydrogen peroxide and the transition metal(s) form a molar ratio of about 20 to about 100.

The hydrolysis catalyst, in some embodiments of the invention, comprises one or more enzymes each with cellulolytic activity and/or hemicellulolytic activity. The one or more enzymes may be present in an amount that results in an enzyme loading of about 0.001 g/kg to about 10 g/kg (mass of total enzymes per mass of the carbohydrate-rich substrate).

In preferred embodiments, the liquid solution in step (a) is provided as, or treated to form, a homogeneous mixture. For example, the process may include mixing the hydrolysis catalyst with process water using turbulent energy to produce the homogeneous mixture. The turbulent energy may be in the range of about 0.5 W/kg to about 5 W/kg.

In various embodiments, the reaction temperature is about 15° C. to about 95° C., the reaction time is about 15 minutes to about 8 hours, and the reaction pressure is about 50 kPa to about 150 kPa, such as about atmospheric pressure (101.325 kPa).

The expulsion time may be about 1 second to about 60 minutes. The expulsion pressure may be from about 100% to about 200% of the water equilibrium pressure at the reaction temperature. In the embodiments, the expulsion temperature is about the same as the reaction temperature.

The number of pressure cycles may vary widely, such as from 1 to about 200. In various embodiments, the number of pressure cycles is 1, 2, 3, 4, 5, 6, 7, 8, 9, 10, 11, 12, 13, 14, 15, 16, 17, 18, 19, 20, 30, 40, 50, 60, 70, 80, 90, 100, or more.

Some preferred embodiments further include, prior to step (a), maintaining a gas pressure above the carbohydrate-rich substrate at an evacuation pressure and for an evacuation time to infuse a hydrolysis catalyst into the carbohydrate-rich substrate at an infusion temperature. In some embodiments, the infusion temperature is less than or equal to the boiling point of water at the evacuation pressure. The infusion temperature may be from about 40° C. to about 90° C., for example. The evacuation pressure is preferably less than the reaction pressure. In some embodiments, the evacuation pressure is from about 105% to about 200% of the water equilibrium pressure at the infusion temperature. The evacuation time may be from about 1 minute to about 2 hours.

Some process embodiments further include controlling pH of the reaction mixture by adjusting gas-phase composition above, or in equilibrium with, the liquid solution. The gas-phase composition may be adjusted by varying the pressure and/or composition of the gas cap (e.g., a $CO_2$-rich gas cap) above the liquid solution.

In certain embodiments, the hydrolysis catalyst comprises an organic acid, a mineral acid, or a combination thereof, and the pH is controlled to about 2 or less. In certain embodiments, the hydrolysis catalyst comprises one or more Fenton or Fenton-like reagents and optionally one or more mineral acids, and the pH is controlled between about 1 to about 6. In other embodiments, the hydrolysis catalyst comprises one or more enzymes each with cellulolytic activity and/or hemicellulolytic activity, and the pH is controlled between about 4 to about 7.

Variations of the invention also provide a method of producing sugar monomers and/or polymers from a carbohydrate-rich substrate having lumen space, the method comprising hydrolyzing the carbohydrate-rich substrate in the presence of a liquid solution containing a hydrolysis catalyst, and cycling gas pressure between a reaction pressure and an expulsion pressure, wherein at the reaction pressure, the sugar monomers and/or polymers are generated within the lumen space, and wherein at the expulsion pressure, the sugar monomers and/or polymers are expelled out of the lumen space and into the liquid solution.

In preferred methods, the mass-transfer rate of the sugar monomers and/or polymers transporting out of the lumen space is higher than the diffusion rate of the sugar monomers and/or polymers diffusing out of the lumen space. In some embodiments, the reaction rate of generation of the sugar monomers and/or polymers is higher than an otherwise-identical process without a step of cycling the gas pressure.

Variations of the invention also provide a system for producing sugar monomers and/or polymers from a carbohydrate-rich substrate having lumen space, the system comprising a reactor configured for hydrolyzing the carbohydrate-rich substrate in the presence of a liquid solution containing a hydrolysis catalyst, to generate sugar monomers and/or polymers within the lumen space; and a pressure-control unit, in operable communication with the reactor, capable of cycling gas pressure between a reaction pressure and an expulsion pressure, wherein the cycling expels the sugar monomers and/or polymers out of the lumen space and into the liquid solution.

Preferred systems also include a mixing unit, in operable communication with the reactor, configured for mixing the hydrolysis catalyst with process water using turbulent energy to produce a homogeneous mixture. Some systems also include a pH-control unit, in operable communication with the reactor, configured to control pH of the reaction mixture by adjusting gas-phase composition above, or in equilibrium with, the liquid solution.

BRIEF DESCRIPTION OF THE DRAWING

FIG. 1 is a schematic drawing of an experimental apparatus used in embodiments and examples of the present invention.

DETAILED DESCRIPTION OF EMBODIMENTS OF THE INVENTION

The methods, processes, and systems of the present invention will be described in detail by reference to various non-limiting embodiments and FIGURE(s).

This description will enable one skilled in the art to make and use the invention, and it describes several embodiments, adaptations, variations, alternatives, and uses of the invention. These and other embodiments, features, and advantages of the present invention will become more apparent to those skilled in the art when taken with reference to the following detailed description of the invention in conjunction with the accompanying drawings.

As used in this specification and the appended claims, the singular forms "a," "an," and "the" include plural referents unless the context clearly indicates otherwise. Unless defined otherwise, all technical and scientific terms used herein have the same meaning as is commonly understood by one of ordinary skill in the art to which this invention belongs.

Unless otherwise indicated, all numbers expressing parameters, conditions, results, and so forth used in the specification and claims are to be understood as being modified in all instances by the term "about." Accordingly, unless indicated to the contrary, the numbers set forth in the following specification and attached claims are approximations that may vary depending upon specific algorithms and calculations.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phase "consisting essentially of" limits the scope of a claim to the specified elements or method steps, plus those that do not materially affect the basis and novel characteristic(s) of the claimed subject matter.

With respect to the terms "comprising," "consisting of," and "consisting essentially of," where one of these three terms is used herein, the presently disclosed and claimed subject matter may include the use of either of the other two terms. Thus in some embodiments not otherwise explicitly recited, any instance of "comprising" may be replaced by "consisting of" or, alternatively, by "consisting essentially of."

No embodiments described herein shall be limited by any theory or speculation regarding reaction mechanisms, mass-transfer mechanisms, or descriptions of feedstocks or products.

Some variations of the present invention are premised on a technical solution to the aforementioned problem that when hydrolyzing biomass to produce sugars, mass transfer of sugars out of the bulk fibers is fundamentally limited when relying on simple diffusion. During or after catalytic hydrolysis that generates dissolved sugars in the fiber lumen (open space within fibers), pressure cycling is utilized to pump out the dissolved sugars into the liquid phase, thereby improving overall product mass transfer out of fiber and improving internal hydrolysis kinetics. The principles of the invention are demonstrated in the Examples herein.

The low diffusion coefficient and relatively long length of the lumen in fibers make it impractical to use diffusion to infuse reagents into fibers or to use diffusion to remove high-molecular-weight sugars from the lumen. Preferred variations of this invention employ vacuum infusion for infusing reagents into the lumen of fibers, and vacuum expulsion for extracting sugars out of the lumen of fibers. Vacuum infusion and vacuum expulsion take on the order of minutes, compared with diffusion which takes days, weeks, or months.

Some variations of this invention can significantly reduce the cost of extracting sugars from biomass by eliminating the costly step of separating the fibers and relocating the lignin on the outside of the fibers. Instead, a homogeneous reagent may be infused under vacuum into the lumen of fibers where there is little lignin to prevent hydrolysis. After hydrolysis in the lumen produces sugars from cellulose and hemicellulose, vacuum may then be used to expand residual bubbles inside fibers to expel sugars from the lumen so they can be recovered.

Variations of the invention provide a method of producing sugar monomers and/or polymers from a carbohydrate-rich substrate having lumen space, the method comprising hydrolyzing the carbohydrate-rich substrate in the presence of a liquid solution containing a hydrolysis catalyst, and cycling gas pressure between a reaction pressure and an expulsion pressure, wherein at the reaction pressure, the sugar monomers and/or polymers are generated within the lumen space, and wherein at the expulsion pressure, the sugar monomers and/or polymers are expelled out of the lumen space and into the liquid solution.

In preferred methods, the mass-transfer rate of the sugar monomers and/or polymers transporting out of the lumen space is higher than the diffusion rate of the sugar monomers and/or polymers diffusing out of the lumen space. In some embodiments, the reaction rate of generation of the sugar monomers and/or polymers is higher than an otherwise-identical process without a step of cycling the gas pressure.

Variations of the invention also provide a system for producing sugar monomers and/or polymers from a carbohydrate-rich substrate having lumen space, the system comprising a reactor configured for hydrolyzing the carbohydrate-rich substrate in the presence of a liquid solution containing a hydrolysis catalyst, to generate sugar monomers and/or polymers within the lumen space; and a pressure-control unit, in operable communication with the reactor, capable of cycling gas pressure between a reaction pressure and an expulsion pressure, wherein the cycling expels the sugar monomers and/or polymers out of the lumen space and into the liquid solution.

Preferred systems also include a mixing unit, in operable communication with the reactor, configured for mixing the hydrolysis catalyst with process water using turbulent energy to produce a homogeneous mixture. Some systems also include a pH-control unit, in operable communication with the reactor, configured to control pH of the reaction mixture by adjusting gas-phase composition above, or in equilibrium with, the liquid solution.

In some variations, the invention provides a process for producing sugar monomers and/or polymers from a carbohydrate-rich substrate, the process comprising the steps of:

(a) providing a reaction mixture comprising a carbohydrate-rich substrate and a liquid solution containing a hydrolysis catalyst;

(b) exposing the reaction mixture to a gas-phase reaction pressure;

(c) maintaining the reaction mixture at a reaction temperature for a reaction time to generate the sugar monomers and/or polymers within lumen space of the carbohydrate-rich substrate;

(d) exposing the reaction mixture to a gas-phase expulsion pressure that is lower than the reaction pressure, to expel the sugar monomers and/or polymers out of the lumen space and into the liquid solution;

(e) maintaining the reaction mixture at an expulsion temperature for an expulsion time;

(f) repeating steps (b) to (e) for a number of pressure cycles; and (g) recovering the sugar monomers and/or polymers.

In some embodiments, the carbohydrate-rich substrate is selected from the group consisting of naturally occurring lignocellulosic biomass, processed lignocellulosic biomass, pulp, paper, paper-based products, carbohydrate-rich industrial waste, and combinations thereof. In certain embodiments, the carbohydrate-rich substrate includes naturally occurring lignocellulosic biomass selected from the group consisting of size-reduced softwood, sugarcane bagasse, wheat straw, corn stover, switchgrass, miscanthus, and combinations thereof. In some embodiments, the carbohydrate-rich substrate includes carbohydrate-rich industrial waste selected from the group consisting of food waste, components of municipal solid waste, and combinations thereof.

Biomass often has little or no economic value, since the low bulk density of biomass (50 to 150 kg/m$^3$) and hydroscopicity of biomass make transport uneconomical. Transporting biomass-derived sugars is much more attractive. The sugars in biomass have a high economic value, but are usually not cost-competitive with sugars from sugarcane, sugar beets, or corn because of the high cost of transporting the biomass, separating the fibers from each other, and then extracting the sugars from the fibers. Some embodiments of this invention make it practical and economical to extract sugars from biomass close to the source of the biomass, and to then transport these higher-bulk-density extracted sugars, thereby significantly reducing the transportation costs per kg of sugar produced.

The preferred embodiments of this invention may utilize three types of reagents: enzyme reagents, dilute-acid reagents, and/or Fenton or Fenton-like reagents. Any of these reagents may be suitable for producing sugar monomers or polymers, including nanocellulose crystals.

Dilute-acid reagents are diluted water solutions of acids (such as sulfuric acid or hydrochloric acid or mixtures thereof) with a pH between generally 0 and 2, preferably between 0.5 and 1. Hydrolysis temperatures at or above 90° C. are typically employed when using dilute-acid reagents. The acids may be inorganic or acid.

In some embodiments, the hydrolysis catalyst comprises an organic acid, a mineral acid, or a combination thereof. For example, the hydrolysis catalyst may comprise sulfuric acid in an amount that results in the liquid solution having a sulfuric acid concentration of about 10 mM to about 200 mM.

Various embodiments employing inorganic acids may utilize sulfuric acid, sulfurous acid, hydrochloric acid, nitric acid, phosphoric acid, hydrogen peroxide, hydrofluoric acid, nitrous acid, hydrazoic acid, or combinations or salts thereof. Various embodiments employing organic acids may utilize acetic acid, acetoacetic acid, citric acid, formic acid, lactic acid, ascorbic acid, benzoic acid, propionic acid, 3-hydroxypropanoic acid, carbonic acid, glycolic acid, glyoxylic acid, glyceric acid, acrylic acid, adipic acid, malonic acid, methylmalonic acid, succinic acid, malic acid, tartaric acid, itaconic acid, mesaconic acid, glutaric acid, or combinations or salts thereof. When a weak acid such as acetic acid is used, a higher concentration will generally be necessary, compared to a stronger acid such as sulfuric acid.

Various embodiments employ Fenton reagents or Fenton-like reagents, composed of a transition metal catalyst in solution with hydrogen peroxide at a pH between about 1 and 6 and a temperature between about 15° C. and 95° C. Reagents containing hydrogen peroxide that reacts with transition metal catalysts to depolymerize cellulose and/or hemicellulose are herein referred to as "Fenton reagents" when based on Fe, and "Fenton-like reagents" when based on another transition metal catalyst. The transition metal catalyst is most commonly Fe(II) or Mn(II), but others may be employed, such as Co, Ni, Mo, Cu, Zn, etc. Depolymerization of cellulose and hemicellulose is herein referred to as hydrolysis, whether the depolymerization is caused by hydrolysis of glycosidic bonds or breaking bonds using a Fenton or Fenton-like reagent.

In some embodiments, the hydrolysis catalyst may comprise one or more Fenton or Fenton-like reagents including hydrogen peroxide and a metal selected from iron, manganese, or combinations thereof. Fenton or Fenton-like reagents may also be provided along with an acid as part of the reagent. Fenton reagents may include solutions of $FeSO_4/H_2O_2$, $FeSO_4/H_2SO_4/H_2O_2$, $FeCl_2/H_2O_2$, or $FeCl_2/HCl/H_2O_2$, and or Fenton-like reagents may include similar compositions based on Mn instead of Fe. In some embodiments, the hydrogen peroxide and the metal form a molar ratio ($H_2O_2$/metal) of about 20 to about 100, such as about 30, 40, 50, 60, 70, 80, or 90. Typically, the Fenton or Fenton-like reagents are adjusted to a pH between 1 and 6 using a mineral acid such as $H_2SO_4$ or HCl. Thus, in some embodiments, the hydrolysis catalyst comprises one or more Fenton or Fenton-like reagents in combination with one or more mineral acids. Fenton or Fenton-like reagents are effective for hydrolyzing at a wide range of temperatures, in a range from about 15° C. to about 95° C., such as about 20° C., 25° C., 30° C., 35° C., 40° C., 45° C., 50° C., 55° C., 60° C., 65° C., 70° C., 75° C., 80° C., 85° C., or 90° C. The optimal compositions and operating conditions of these reagents for hydrolyzing different types of carbohydrate-rich material such as, but not exclusively, lignocellulosic biomass are known to those skilled in the art.

A description of using Fenton reagents to depolymerize cellulose in a pH range of 3 to 5 and a temperature up to 100° C. is in Heijnesson-Hultén, "Method of preparing microfibrillar polysaccharide," U.S. Pat. No. 7,700,764, issued Apr. 20, 2010, which is hereby incorporated by reference herein. A description of the kinetics of the Fenton reaction as a function of pH and temperature is in Khamaruddin et al., "Using Fenton's reagents for the degradation of diisopropanolamine: effect of temperature and pH," *International conference on environment and industrial innovation*, Singapore, 2011, which is hereby incorporated by reference herein. A description of the effectiveness of using Fenton reagents at high temperatures and pH 1.7 is in de Tuesta et al., "Application of high-temperature Fenton oxidation for the treatment of sulfonation plant wastewater," *Journal of Chemical Technology and Biotechnology* (2014), which is hereby incorporated by reference herein.

The hydrolysis catalyst, in some embodiments, comprises hydrogen peroxide, without necessarily a transition metal present or added. In some embodiments, a method includes infusing only hydrogen peroxide without adding any transition metal catalyst. The transition metal catalysts may be absorbed in the lumen in a pretreatment step, for example, and then only hydrogen peroxide is introduced as a reagent to react with the transition metal catalysts which have been already absorbed in the lumen in the pretreatment step. It will also be recognized that transition metals naturally occur in the biomass, and these native transition metals may be effective to form in situ Fenton or Fenton-like reagents. In some embodiments, biomass may be deconstructed with only hydrogen peroxide under suitable conditions.

The hydrolysis catalyst, in some embodiments of the invention, comprises one or more enzymes each with cellulolytic activity and/or hemicellulolytic activity. Enzyme reagents are preferably combinations of enzymes with cellulolytic activities (mainly cellulase and hemicellulase enzymes) with operating pH preferably between 4.5 and 6.5, and hydrolysis temperatures typically between 40° C. and 50° C. Enzyme concentration may vary from milligrams to grams of enzyme per kg of substrate, depending on the enzyme type and operating conditions. The one or more enzymes may be present in an amount that results in an enzyme loading of about 0.001 g/kg to about 10 g/kg (mass of total enzymes per mass of the carbohydrate-rich substrate).

In preferred embodiments, the liquid solution in step (a) is provided as, or treated to form, a homogeneous mixture. For example, the process may include mixing the hydrolysis catalyst with process water using turbulent energy to produce the homogeneous mixture. The turbulent energy may be in the range of about 0.5 W/kg to about 10 W/kg, such as about 5 W/kg.

In some embodiments, concentrated reagents are first homogenized with process water using turbulent energy to form a homogeneous reagent. Sufficient turbulent energy is used so that the Kolmogorov length scale is on the order of less than the lumen diameter (e.g., about 20 microns). Reagents can be any substance with adequate cellulolytic and hemicellulotytic activity, natural or artificial, of biological or chemical origin, pure or in combinations such as organic and mineral acids (e.g. sulfuric acid), enzymes (e.g. cellulase and hemicellulases), Fenton or Fenton-like reagents, pure hydrogen peroxide, or any other suitable substance.

Some processes first homogenize one or more selected reagents with process water, using turbulent energy for mixing to produce a homogeneous reagent. Using the Kolmogorov length scale, and since the kinematic viscosity of water at 20° C. is about $10^{-6}$ m$^2$/s, the energy required to mix the reagents and process water to a 20-micron scale is about 6.25 W/kg. This is very modest mixing energy compared to the amount of mechanical mixing energy typically used in biomass hydrolysis by conventional methods. At higher temperatures, even less mixing energy is required.

Those skilled in the art will recognize that there are many simple mixing devices than can mix with this kind of energy. One such simple mixing device is a 25-mm diameter plastic pipe 8 meters long with a pipe roughness of 0.0014, infusing from atmospheric pressure (100 kPa) to a vacuum of 20 kPa with a 2.8 liter/sec (6 CFM) vacuum pump maintaining the vacuum during infusion. The power dissipated in the pipe due to pressure drop is 226.4 W. The total amount of liquid in the pipe is 4.05 kg, so the power dissipated per kg is about 56 W/kg, which is significantly more power than is needed to mix at a 20-micron scale (the exemplary flow rate is sufficient to infuse 18 m$^3$ in 1.8 hours).

Some preferred embodiments further include, prior to step (a), maintaining a gas pressure above the carbohydrate-rich substrate at an evacuation pressure and for an evacuation time to infuse a hydrolysis catalyst into the carbohydrate-rich substrate at an infusion temperature. In some embodiments, the infusion temperature is less than or equal to the boiling point of water at the evacuation pressure. The infusion temperature may be from about 40° C. to about 90° C., for example. The evacuation pressure is preferably less than the reaction pressure. In some embodiments, the evacuation pressure is from about 105% to about 200% of the water equilibrium pressure at the infusion temperature. The evacuation time may be from about 1 minute to about 2 hours.

When a vacuum is applied to the starting biomass, the homogenized reagent is infused into the biomass under vacuum. Because this infusion (in some embodiments) is done under vacuum, the reagents are rapidly and evenly distributed among the fibers and the biomass. When the vacuum is removed, the reagents are drawn into the lumen of the fibers.

The temperature of the homogeneous reagent should be low enough so the water in the homogeneous reagent does not boil at the infusion pressure, where boiling entails the fast release of vapor as large bubbles. It can also be important that the temperature is kept below the equilibrium temperature at the pressure. Since water is normally the main constituent of the homogeneous reagent, water equilibrium data can be used to determine the operating temperature at a given pressure and vice versa. For instance, if the infusion temperature of the homogeneous reagent is about 55° C., the infusion pressure should be more than about 20 kPa. A consequence of this is that when using dilute acid hydrolysis at 90° C., the infusion temperature of the homogeneous reagent (e.g., sulfuric acid solution) should be less than about 55° C. if the infusion pressure is about 20 kPa, and the temperature must be raised to about 90° C. after infusion of the homogeneous reagent.

In various embodiments, the reaction temperature is about 15° C. to about 95° C., such as about 20° C., 25° C., 30° C., 35° C., 40° C., 45° C., 50° C., 55° C., 60° C., 65° C., 70° C., 75° C., 80° C., 85° C., or 90° C. In various embodiments, the reaction time is about 15 minutes to about 8 hours, such as about 30 minutes or 1, 2, 3, 4, 5, 6, or 7 hours. In various embodiments, the reaction pressure is about 50 kPa to about 150 kPa, such as about atmospheric pressure (101.325 kPa), or about 60, 70, 80, 90, 100, 110, 120, 130, or 140 kPa.

The expulsion time may be about 1 second to about 60 minutes, such as about 10, 30, or 60 seconds or about 2, 5, 10, 15, 20, 25, 30, 35, 40, 45, 50, or 55 minutes. The expulsion pressure may be from about 100% to about 200% of the water equilibrium pressure at the reaction temperature. In the embodiments, the expulsion temperature is about the same as the reaction temperature, but the expulsion temperature may be lower or higher than the reaction temperature.

The number of pressure cycles may vary widely, such as from 1 to about 200. In various embodiments, the number of pressure cycles is 1, 2, 3, 4, 5, 6, 7, 8, 9, 10, 11, 12, 13, 14, 15, 16, 17, 18, 19, 20, 30, 40, 50, 60, 70, 80, 90, 100, or more. The pressure cycling may be done periodically, continuously, or semi-continuously. The length of time between pressure cycles may vary. Specific pressure profiles may be employed, if desired. For example, a fixed reaction pressure alternating with a declining expulsion pressure may be utilized. Or the cycle time may increase or decrease over time, and so on.

A vacuum is periodically applied (i.e. after each pressure cycle) to the mixture to pump the now-dissolved sugar-rich solution out of the lumen and mix the solution with the homogeneous reagent outside the fibers, where the sugars are diluted. When the vacuum is removed, homogeneous reagent with a lower concentration of sugars is pumped back into the lumen. When hydrolysis completes, a vacuum may be applied to the mixture to pump the sugars out of the lumen, and the liquid may be drained from the biomass while under vacuum.

As used herein, a sugar "polymer" means a chain of sugar molecules with a degree of polymerization of at least two. Sugar "oligomers" (generally with degree of polymerization of 2 to about 8) may be produced, and/or longer polymers (e.g., with degree of polymerization of about 8 or higher) may also be generated and extracted. Sugar monomers or polymers may be completely dissolved into solution, or suspended in solution.

The sugar monomers and/or polymers may include hexose sugars in monomer, oligomer, or polymer form, including one or more of glucose, mannose, galactose, O-acetyl galactoglucomannan, and nanocellulose crystals. The sugar monomers and/or polymers may also include pentose sugars in monomer, oligomer, or polymer form, including xylose and/or arabinose. Some embodiments preferentially produce monomeric sugars, which are more fermentable than polymeric sugars, while some embodiments preferentially produce polymeric sugars, because of the significantly higher value of polymeric sugars.

As cellulose and hemicellulose are depolymerized, the fragments become detached from the biomass and become more miscible with water. Monomeric and oligomeric sugars are very soluble in water, and some high-molecular-weight polymeric sugars such as O-acetyl-galactoglucomannan from softwood are also very soluble in water. The depolymerization of cellulose in the amorphous regions to produce nanocellulose is described in Nelson, "Apparent activation energy of hydrolysis of some cellulosic materials," *Journal of Polymer Science* 43 142 (1960): 351-371, which is hereby incorporated by reference herein.

Nanocellulose crystals (also known as nanocrystalline cellulose or cellulose nanocrystals) are made from acid hydrolysis of the amorphous regions of cellulose fibrils and have a length of 100-600 nm and a diameter of 2-20 nm. According to Peng et al., "Chemistry and applications of nanocrystalline cellulose and its derivatives: a nanotechnology perspective," *The Canadian Journal of Chemical Engineering* 89 5 (2011): 1191-1206, which is hereby incorporated by reference herein, sulfuric and hydrochloric acids are extensively used in the preparation of nanocellulose crystals. Due to the abundance of charged sulfate groups on its surface, nanocellulose crystals obtained from sulfuric acid hydrolysis disperse readily in water, while those produced from hydrochloric acid hydrolysis do not disperse as readily, and their aqueous suspensions tend to flocculate (Peng et al.). For this reason, preferred embodiments of this invention, when producing nanocellulose crystals, use sulfuric acid.

The main high-molecular-weight polymers of sugars from biomass are nanocellulose crystals (69 kDa), O-acetyl galactoglucomannan (20 kDa), arabinoxylan (300 kDa), arabinogalactan (40 kDa), and xyloglucan (470 kDa). High-molecular-weight polymers of sugars diffuse quite slowly in water, with an average diffusion coefficient at 25° C. of about $10^{-11}$ m$^2$/s. When diffusing into or out of softwood chips, the diffusion coefficient is reduced by about 40% to account for the tortuosity of the diffusion path, with a similar reduction with other types of biomass. Given an average wood chip size of 12 mm, and given that diffusion takes place from both ends of a wood chip, diffusion of high-molecular-weight polymers of sugar 6 mm out of a wood chip takes about $(0.006$ m$)^2/(10^{-11}$ m$^2$/s$)/0.40=9\times10^6$ seconds or about 104 days. Similarly, it takes about 19 hours for sulfuric acid to diffuse into a wood chip and 1.8 days for glucose to diffuse out of the center of a wood chip. Raising the temperature from 25° C. to 50° C. approximately doubles the diffusion coefficient, and raising the temperature from 25° C. to 90° C. approximately quadruples the diffusion coefficient, but the time scales for diffusion into or out of fibers are still too long to be practical.

In some embodiments, a vacuum is applied to the biomass and the homogeneous reagent is infused into the fibers under vacuum. In certain embodiments, fibers are infused by maintaining a vacuum while letting the homogeneous reagent be drawn into the reaction vessel at the bottom. When using dilute-acid hydrolysis, high-molecular-weight polymers of cellulose and glucose will be solubilized in the lumen. These need to be expelled periodically from the lumen by applying a vacuum to the mixture. Once the hydrolysis has completed, the sugar solution may be extracted from the lumen of the fibers by applying a vacuum and draining the sugar solution from the biomass.

Some process embodiments further include controlling pH of the reaction mixture by adjusting gas-phase composition above, or in equilibrium with, the liquid solution. The gas-phase composition may be adjusted by varying the pressure and/or composition of the gas cap (e.g., a $CO_2$-rich gas cap) above the liquid solution.

In certain embodiments, the hydrolysis catalyst comprises an organic acid, a mineral acid, or a combination thereof, and the pH is controlled to about 2 or less. In certain embodiments, the hydrolysis catalyst comprises one or more Fenton or Fenton-like reagents, and the pH is controlled between about 2 to about 6 (such as about 2 to 4). In other embodiments, the hydrolysis catalyst comprises one or more enzymes each with cellulolytic activity and/or hemicellulolytic activity, and the pH is controlled between about 4 to about 7.

Accurate pH control is well-known to be a key requirement for effective hydrolysis of biomass. Depending on the nature of the reagent(s) used, different approaches may be used. In the case of dilute acids, these reagents will be dosed in sufficient quantity to bring the pH to the lower level (such as between 1 and 3) for effective hydrolysis. The acids are typically strong enough to counteract the effect of other pH-influencing substance that may be present.

When using enzymes, the requirements are more complex. In particular, a key characteristic of cellulase and hemicellulase enzymes is that they hydrolyze cellulose and hemicellulose in a narrow range of pH, below neutrality. When using pure cellulose or hemicellulose after lignin has been removed, the optimal pH is around 5. However, when there is lignin that can absorb these enzymes, the optimal pH is around 6. This is described in Lan et al., "Enzymatic saccharification of lignocelluloses should be conducted at elevated pH 5.2-6.2," *BioEnergy Research* 6 2 (2013): 476-485, which is hereby incorporated by reference herein.

The maintenance of this level of pH may be challenging as often the substrate may contain materials which tend to increase the pH above the desirable range. For instance, calcium carbonate is often used as a paper coating, and is present in high concentrations in waste paper. When dissolved in water, calcium carbonate makes water more alkaline, often well above pH 8, with the solubility of calcium carbonate decreasing with increasing temperature. This effect can be counteracted by buffering the reagent solution with a weak or mild acid which lowers the pH. An effective weak acid is carbonic acid which may be formed by the dissolution of carbon dioxide ($CO_2$) in water. By controlling the composition of the gas cap over the homogeneous reactant—for instance, by providing a gas cap rich in $CO_2$ or completely composed of $CO_2$—the amount of carbonic acid in solution may be controlled to effectively buffer the solution against the effect of alkalinizing agents. When water is saturated with calcium carbonate, and when the partial pressure of carbon dioxide in water is 10 kPa (0.1 atm), the pH of water is 6.63 and when the partial pressure is 100 kPa (1.0 atm), the pH of the solution is 5.96. When the partial pressure of carbon dioxide is that of the atmosphere (35 Pa, $3.5 \times 10^{-4}$ atm), the pH of the solution is 8.27. Hence, by controlling the amount of $CO_2$ in the gas cap and/or the $CO_2$ partial pressure, one can control the pH, even in conditions of saturation with calcium carbonate.

The pH of the homogeneous reagent should be maintained around 1 to 2 when using dilute-acid hydrolysis. In some embodiments, a homogeneous reagent at 90° C. contains between 10 mM (pH 1.97) and 200 mM (pH 0.80) sulfuric acid. A pH of about 1 hydrolyzes about 10 to 20 times faster than a pH of about 2. The kinetics of dilute acid hydrolysis are described in Lenihan et al., "Kinetic modelling of dilute acid hydrolysis of lignocellulosic biomass," *Biofuel production— recent developments and prospects*, InTech, Croatia (2011): 293-308, which is hereby incorporated by reference herein.

Neutralizing the dilute sulfuric acid sugar solution with calcium carbonate produces 1.4 kg of calcium sulfate (gypsum) for every kg of sulfuric acid. Calcium sulfate has a solubility of 0.255 g/L at 20° C. and 0.22 g/L at 90° C. A 100 mM solution of sulfuric acid will precipitate about 13.4 g/L of calcium sulfate when neutralized with calcium carbonate. More of the calcium sulfate is precipitated from the sugar solution after concentration and further separated by filtration. Calcium sulfate is non-toxic and can also be used as a soil improver. A solution of calcium sulfate has a pH of about 7.

In some embodiments, a sulfuric acid solution is neutralized with sodium hydroxide, producing sodium sulfate. Sodium sulfate is much more soluble in water than calcium sulfate and is similarly non-toxic. A solution of sodium sulfate has a pH of about 7.

A person of ordinary skill in the art will recognize that known apparatus may be employed for the processes, systems, and methods disclosed herein. The processes herein may be batch, continuous, semi-continuous, or pseudo-continuous. Any reference to "vessel" or "reactor" herein shall be construed to mean one or a plurality of such apparatus (such as in series or in parallel). Various flow patterns may be desired or observed. With chemical reactions and simultaneous mass-transfer processes involving multiple phases, the fluid dynamics can be quite complex. Depending on the specific design, flow patterns may approach plug flow or well-mixed mixed flow.

The throughput, or process capacity, may vary widely from small laboratory-scale units to full commercial-scale biorefineries, including any pilot, demonstration, or semi-commercial scale. In various embodiments, the process capacity is at least about 1 kg/day, 10 kg/day, 100 kg/day, 1 ton/day (all tons are metric tons), 10 tons/day, 100 tons/day, 500 tons/day, 1000 tons/day, 2000 tons/day, or higher.

The overall system may be at a fixed location, or it may be made portable. The system may be constructed using modules which may be simply duplicated for practical scale-up.

Various probes may allow precise process monitoring and control across various stages of the process, up to and potentially including all stages of the process. Precise process monitoring would be expected to result in yield and efficiency improvements, both dynamically as well as over a period of time when operational history can be utilized to adjust process conditions (including pressure cycling programs). In some embodiments, a reaction probe is disposed in operable communication with a process zone. Such a reaction probe may be useful to extract liquid samples and analyze them, in order to determine extent of hydrolysis, or sugar profile, etc. Process adjustments may be based on measurements, if deemed necessary or desirable, using well-known principles of process control (feedback, feedforward, proportional-integral-derivative logic, etc.).

Solid, liquid, and gas streams produced or existing within the process can be independently recycled, passed to subsequent steps, or removed/purged from the process at any point.

EXAMPLES

The following experiments demonstrate the principles of this invention. The pressure cycling described above has been shown, by experimental evidence, to be useful for producing sugar monomers and/or polymers from a carbohydrate-rich substrate.

The experimental apparatus of FIG. 1 is designed to reproduce industrial process functionality as far temperature, pressure, and flow control of an industrial unit. It differs from an industrial unit in the loading and unloading of the biomass (the sample). The experimental apparatus is used in all examples below, except for Example 1 which uses a Buchner flask to infuse water into several types of biomass.

With reference to FIG. 1, the experimental apparatus 100 consists of a main infusion vessel 102, which under operation is kept almost completely immersed inside a thermostatic bath 101 which can operate over a wide range of temperature and whose precise temperature control is ensured by a temperature controller 114. The infusion vessel 102 is closed with a removable and sealed lid 118. The infusion vessel 102 and the sealed lid 118 are designed to be able to hold and sustain vacuum conditions as required by the process conditions. The desired amount of sample material 117 (bone dry or as is) can be placed inside the infusion vessel 102. The infusion vessel 102 can be supplied with $CO_2$ via a $CO_2$ cylinder 106 and a $CO_2$ line 107. On the $CO_2$ line 107, a flow/pressure regulator 108 is used to set the pressure at which the $CO_2$ is delivered to the infusion vessel 102. A vacuum pump 103 is used to evacuate and maintain vacuum inside the infusion vessel 102. A pressure indicator 116 and temperature indicator 119 are installed on the infusion vessel 102. The infusion vessel 102 is connected through a gate valve 109 to a container 105 with prepared homogeneous reagent. The vacuum pump 103 is connected to the infusion vessel 102 via a line where a pressure regulator 110 is installed. The pressure regulator 110 allows the infusion vessel 102 pressure to be regulated over a wide range of vacuum levels, while the vacuum pump 103 is operated at constant speed. A four-way valve 104 on the gas outlet of the infusion vessel 102 allows one to remove samples from the sample port 111, insulate the infusion vessel 102, cycle the pressure 116, and recycle part of the sample back into the infusion vessel 102 without altering the pressure and the gas cap composition inside it.

The experimental procedure for Examples 2 to 7 is as follows. $CO_2$ is used in the gas cap to control the pH of the reacting mixture. In the case of using diluted acid hydrolysis, any other gas (including air), inert or not, may be used in the gas cap, the experimental procedure being same. Premixed and pH-buffered aqueous solution is prepared separately according to the specific needs of the experiment; optionally the aqueous solution may be preheated to a temperature of interest. The biomass sample is placed inside the infusion vessel 102. No liquid is present in the infusion vessel 102. Typically the sample is placed inside the infusion vessel as-is and no drying is performed. The infusion vessel 102 is placed in thermostatic bath 101, which is operating at the temperature set for the experiment. Once the lid 118 is placed on top of the infusion vessel 102, using the vacuum pump 103 and $CO_2$ from the line 107, any air is flushed and a $CO_2$ atmosphere is formed on top of the sample. Once the flushing of any residual air is ensured, the flow of fresh $CO_2$ from the line 107 is interrupted by operating on the flow controller 115. The pressure in the infusion vessel 102 is allowed to drop to the level defined in the experiment by controlling it via the pressure regulator 110.

Once pressure and temperature are stabilized at the desired level, the gate valve 109 is opened and the premixed homogeneous reagent is allowed to enter the infusion vessel 102 where the infusion takes place. The amount of sample material is set in such a way that, depending upon the bulk density of the material, the sample is completely submerged once the feeding of the liquid is interrupted. By accurately selected temperature and pressure, boiling of the liquid can be avoided (boiling causes large release of gas bubbles). After the infusion is completed and the gate valve 109 is closed, a partial pressure of one atm of $CO_2$ is established by opening and regulating the flow and pressure controller 108.

The experiment then can proceed for the duration desired. If a liquid sample is needed during the experiment, a syringe may be connected to the four-way valve 104 sample port 111 which is set as to allow the syringe to be filled with liquid. Any residual liquid flows back into the vessel through the four-way valve manifold once the syringe is removed and the sample port 111 is closed.

This experimental set-up allows cycling the pressure. If pressure cycle is desired, the flow and pressure controller 108 is closed and the four-way valve 104 is open to the line into the vacuum pump 103. The pressure level is regulated by setting the pressure regulator 110. Upon reaching the desired low pressure, this is maintained for the desired time and then the four-way valve 104 is closed to isolate the vacuum line and the flow and pressure controller 108 is open again to allow $CO_2$ to flow inside the infusion vessel 102 and to reestablish a higher partial pressure. During the procedure, the gas cap remains composed of primarily $CO_2$ and any water vapor that may in equilibrium. Upon completing the experiment, the removable lid 119 is lifted and liquid and solids contents are removed for analysis and further treatment. Before any further analysis is carried out, however, the samples are rapidly cooled with ice water to stop any hydrolysis.

Analytical methods used to determine dissolved sugar concentration are either diffractometric analysis or spectrophotometric absorbance using the Dinitrosalicylic Acid assay (DNS Assay) to determine the concentration of dissolved reducing sugar as described in the US Department of Energy, National Renewable Energy Laboratory Technical Report NREL/TP-510-42628 issued on January 2008, which is hereby incorporated by reference herein. Since both methods are optical methods and will be affected by the presence of suspended solids, even when fine, samples are centrifuged at high speed (14,000 RPM) for five minutes in a laboratory centrifuge before being analyzed.

Example 1

Demonstration of Vacuum Infusion and Expulsion

A 500-mL Buchner flask is used with a stopper with a valve that when opened, pulls water slowly into the flask while maintaining a vacuum pressure. A 10 mm length of straw is placed at the bottom of the flask and a coin is positioned on top of it. Then a vacuum pump reduces the pressure to 16 kPa and is held at this pressure for 5 minutes. Approximately 200 mL of water is then poured into the flask under a 16 kPa pressure. Then the pressure is brought back to 100 kPa for 5 minutes. The coin is shaken off the straw and the straw stays at the bottom of the flask. The pressure is reduced to 16 kPa and the straw floats to the top. When the pressure again increases to 100 kPa, the straw sinks. This is repeated 10 times, with the straw alternatively floating and sinking almost immediately after the pressure is changed.

Similarly, a 12 mm wood cube of dry pine is placed at the bottom of the flask and a coin is positioned on top of it. Then a vacuum pump reduces the pressure to 16 kPa and this pressure is held for 10 minutes. Approximately 200 mL of water is then poured into the flask under a 16 kPa pressure, and the pressure is brought back to 100 kPa for 15 minutes. The coin is shaken off the wood cube and the wood cube stays at the bottom of the flask. The pressure is reduced to 16 kPa and the wood cube immediately floats to the top and when the pressure again increases to 100 kPa, the wood cube sinks after a delay of about 15 seconds. This is repeated 10 times, with the wood cube alternatively quickly floating and slowly sinking after the pressure is changed.

The same test with a wood cube is performed, except that the initial vacuum pressure is maintained for 30 minutes instead of 10 minutes. The result is the same, except that there is a delay of about 5 seconds before sinking instead of a delay of about 15 seconds before sinking.

This Example 1 shows that it is possible to use vacuum infusion to infuse a solution into the lumen of lignocellulosic biomass and to use vacuum expulsion to expel a solution from the lumen of lignocellulosic biomass.

Example 2

Process Demonstration with Enzymatic Hydrolysis

A commercially available cellulase enzyme is provided by the manufacturer (Novozymes) in powder form. The apparatus is described above (FIG. 1). Enzyme is added to water in sufficient quantity to ensure that once in contact with 50 grams of substrate (dry basis), the overall dry solid in the system is 15 wt %. The substrate is paper. To represent typical mixes of recycled paper, the sample is 50% office paper (Kraft pulp) and 50% newsprint paper (mechanical pulp).

Enzymes are added at the specific loadings of 0.05, 0.11, and 0.17 gram of enzyme per gram of substrate, where the substrate is the cellulose fraction of the paper sample. These enzyme amounts are added in three solutions of distilled water, carbonated water, and carbonated water with added calcium carbonate.

An experiment is carried out by having three samples of substrate hydrolyzed over an 8-hour period. Samples are taken at 4, 6 and 8 hours with the last sample also terminating the experiment. The results are shown in Table 1, where the first row indicates various enzyme loadings and the first column the hours at which the samples were taken. The numbers in Table 1 indicate the concentration of sugar in the water, expressed in grams per liter. When compared to a control group (not shown) based on the same experiment carried out without enzyme addition, enzymatic hydrolysis is confirmed in these experiments. Temperature is maintained constant at 40° C. for the duration of the experiment.

TABLE 1

Sugar Concentration vs. Time at Different Enzyme Loadings (Example 2)

| Hours | Enzyme Loading* 0.05 g/g | Enzyme Loading* 0.11 g/g | Enzyme Loading* 0.17 g/g |
|---|---|---|---|
| 4 | 13.17 g/L | 23.54 g/L | 29.87 g/L |
| 6 | 13.17 g/L | 26.69 g/L | 35.20 g/L |
| 8 | 17.29 g/L | 28.81 g/L | 36.27 g/L |

*Enzyme loading is based on grams enzymes per grams substrate

Example 3

Process Demonstration with pH Control

As discussed above, pH control is a key difficulty in enzymatic hydrolysis. Proper buffering of the solution is important, as the lack of physical mixing during and after the infusion makes it difficult to adjust the pH by chemical addition. In particular, the hydrolysis of waste paper generates a highly basic environment if pH buffering is missing. This is due to the extensive use of calcium carbonate ($CaCO_3$) in typical paper. Calcium carbonate is used both as a filler and to protect paper from degradation due to acidification. A high solid content water/paper solution will typically have pH around 8 without any buffering, and this is too high for effective enzyme activity.

In this set of experiments, buffering is provided by three alternative methods. In the first method, no buffering is provided in the water, completely relying on the $CO_2$ gas cap in the system to buffer the solution thanks to dissolution of $CO_2$ into the liquid. In the second method, carbonated water is employed. The water being pre-saturated with carbon dioxide will ensure that equilibrium conditions are reached more rapidly, upon the gas cap being applied. In the third method, besides pre-saturating the water with $CO_2$, saturated calcium carbonate is added. This method should remove any uncertainty related to the possible amount of calcium carbonate, which is brought into solution by the paper. Since the water is already at saturation with calcium carbonate, any addition is irrelevant to the equilibrium pH level when the water is also in equilibrium with gas phase $CO_2$ at 1 atm of partial pressure.

In the first case the buffer is provided only by the partial pressure of $CO_2$ in the gas cap of the infusion vessel during the hydrolysis. In the second case, the water has also been saturated with $CO_2$ by carbonation before the infusion. In the third case, the carbonated water has also been saturated with calcium carbonate. The amount of calcium carbonate added is such as to ensure saturation at the operating condition of the infusion.

The final solution pH with only a $CO_2$ gas cap is measured to be 6.5. When carbonation of water is also employed along with a $CO_2$ gas cap, the measured pH is 5.7. When a $CO_2$ gas cap with carbonation as well as $CaCO_3$ addition is utilized, the measured pH is 6.1.

The use of buffered solution in combination with a high partial pressure of $CO_2$ in the gas cap is proven effective to control the pH in a range amenable to hydrolysis by cellulose enzymes, as demonstrated by the final pH recorded upon completion of the hydrolysis after the water solution is completed. In all cases, the result compares favorably with the pH of the unbuffered solution, which is around 8.

Example 4

Process Demonstration with Enzymatic Hydrolysis

When water and solids are separated after the experiment of Example 2, the liquid recovery amounted to only about 50% of the water added, with the remainder being adsorbed by the substrate sample. As the most effective enzymatic hydrolysis will be carried out in close vicinity of the fiber, and the infusion will bring large amount of enzyme inside the fiber lumen, it is suspected that dissolved sugars may remain inside the fiber and do not have way to be removed from the bulk of the liquid when only diffusion is relied upon. To test this concept, two sets of experiments are conducted, both equivalent to Example 2 using water with no addition other than the enzyme, and for a duration of four hours.

Upon completing the experiment, in one case the water is removed and then the analysis is done as in Example 2. In a second set of experiments, the residual biomass is pulped (mechanically refined) and the water is separated by filtration only, after the residual cellulosic material has been thoroughly pulped. In this way, the dissolved sugar concentration is expected to have homogenized across the liquid mass, and any dissolved sugar embedded inside the fiber is expected to have been released. Temperature is maintained constant at 40° C. for the duration of the experiment.

The results are shown in Table 2. This result indicates that there is a considerable amount of extra dissolved sugar trapped in the fiber, consistent with deep penetration of enzymes inside the fiber as postulated by the principles set forth herein.

TABLE 2

Sugar Concentration (4 Hours) at Different Enzyme Loadings (Example 3)

| | Enzyme Loading* 0.05 g/g | Enzyme Loading* 0.11 g/g | Enzyme Loading* 0.17 g/g |
|---|---|---|---|
| No Pulping | 13.17 g/L | 23.54 g/L | 29.87 g/L |
| Pulping | 17.29 g/L | 29.87 g/L | 38.42 g/L |

*Enzyme loading is based on grams enzymes per grams substrate

Example 5

Process Demonstration with Pressure Cycling

Having determined in Example 4 that lacking mechanical mixing, sugar produced by enzymatic hydrolysis inside the fiber may not be removed effectively by simple dewatering, pressure cycling is utilized to demonstrate that cycling the pressure during the hydrolysis process enhances mass transfer and helps remove dissolved sugar from the lumen into the bulk of the liquid mass. In this experiment, a carbonated and calcium carbonate saturated buffer solution is used. The enzyme loading is 0.022 g of enzyme (as is) per grams of substrate. Temperature is kept at 40° C. and infusion is carried out at two pressures, 58 kPa and 16 kPa. After infusion, the pressure is restored to ensure 100 kPa of total pressure with the $CO_2$ gas cap.

In the experiments without pressure cycling, a liquid sample is taken from the infusion vessel without any change in the pressure of the gas cap, which is kept constant through the pressure regulator 108 on the $CO_2$ line 107. In the experiments with pressure cycling, just prior of the sample being taken, the pressure is cycled by applying a 16 kPa vacuum pressure for 5 minutes and then re-establishing the regular 100 kPa pressure. The sample is taken after 100 kPa pressure is re-established. Table 3 shows the amount of sugar in the liquid (g/L) for four cases: 58 kPa infusion with no pressure cycling, 16 kPa infusing with no pressure cycling, 58 kPa infusing with pressure cycling, and 16 kPa infusing with pressure cycling.

Table 3 shows that, in this case, the rate of sugar production is independent of the infusion pressure if no pressure cycling is performed, and that more sugar is produced with 16 kPa infusion than 58 kPa infusion if pressure cycling is performed. This verifies that the pressure cycling of this invention results in a higher rate of sugar production than without pressure cycling, and that a lower infusion pressure results in a higher rate of sugar production than with a higher infusion pressure. Without being bound by theory, this result is consistent with the theory that pressure cycling results in the liquid in the lumen being expelled and mixed with the water outside the lumen.

TABLE 3

Sugar Concentrations (g/L) without and with Pressure Cycling (Example 5)

| Time (hr) | 58 kPa, No Cycling | 16 kPa, No Cycling | 58 kPa, Cycling | 16 kPa, Cycling |
|---|---|---|---|---|
| 0 | 0 | 0 | 0 | 0 |
| 0.25 | 2 | 2 | 4 | 4 |
| 0.5 | 4 | 3 | 4 | 6 |
| 0.75 | 5 | 5 | 5 | 7 |
| 1 | 5 | 5 | 5 | 7 |
| 1.25 | 5 | 6 | 6 | 7 |
| 1.5 | 6 | 6 | 7 | 8 |
| 2 | 7 | 7 | 8 | 9 |
| 2.5 | 7 | 7 | 8 | 9 |
| 3 | 7 | 7 | 8 | 9 |
| 3.5 | 8 | 8 | 9 | 10 |
| 4 | 9 | 9 | 10 | 11 |
| 4.5 | 9 | 10 | 11 | 12 |
| 5 | 11 | 11 | 12 | 13 |
| 6 | 12 | 11 | 13 | 15 |
| 7 | 13 | 13 | 14 | 16 |
| 8 | 14 | 14 | 15 | 17 |

Example 6

Process Demonstration with Varying Acid Concentration

Pressure cycling with varying amounts of sulfuric acid is used to demonstrate that cycling the pressure during the hydrolysis process helps remove dissolved sugar from the lumen into the bulk of the liquid mass. In this experiment, water with 0, 18, and 180 mM sulfuric acid is infused at 16 kPa into softwood shavings. The water is infused at 50° C. After infusion, the pressure is restored to 100 kPa and the 90° C. water bath raises the solution temperature to 90° C. At different times, the pressure is reduced to about 70 kPa for 5 minutes so that the water boils, then the pressure is rapidly raised to 100 kPa and a sample is taken. Table 4 below shows the amount of sugar in the liquid (g/L) for three different sulfuric acid concentrations.

Table 4 confirms that the sugar concentration slowly increases when only hot water is infused. After 2 hours, in 400 mL of water, there is 3 g/L, or a total of 1.2 g of sugar from 50 g of wood shavings, or about 24 mg/g of wood. This is actually about 4 times as much sugar extracted in 2 hours than the 6 mg/g spruce wood described in Azhar et al., "Extraction of hemicelluloses from fiberized spruce wood," *Carbohydrate polymers* 117 (2015): 19-24, which is hereby incorporated by reference herein. This confirms that the vacuum cycling with just 90° C. water (no acid added) removes O-acetyl galactoglucomannan more effectively than from fiberized spruce wood.

TABLE 4

Sugar Concentrations (g/L) for Different Acid Concentrations (Example 6)

| Time (hr) | 0 mM $H_2SO_4$ | 18 mM $H_2SO_4$ | 180 mM $H_2SO_4$ |
|---|---|---|---|
| 0.00 | 0 | 0 | 0 |
| 0.25 | 1 | 1 | 2 |
| 0.75 | 1 | 2 | 6 |
| 1.00 | 1 | 3 | 8 |
| 1.25 | 3 | 3 | 11 |
| 1.50 | 3 | 4 | 12 |
| 2.00 | 3 | 5 | 15 |
| 2.50 | 4 | 5 | 18 |
| 3.00 | 3 | 5 | 20 |
| 3.50 | 3 | 5 | 20 |
| 19.00 | 4 | 11 | 39 |
| 20.00 | 4 | 10 | 39 |
| 27.00 | 4 | 13 | 42 |

The pH of the 18 mM solution of sulfuric acid in wood shavings is 1.62 and the pH of the 180 mM solution is 0.77, a pH difference of about 0.85. The 18 mM solution takes 27 hours to reach 13 g/L sugar, while the 180 mM solution takes about 1.75 hours to reach 13 g/L sugars. This is a ratio of about 15 times longer when the pH difference is 0.85, which is comparable to the kinetics for dissolution of galactoglucomannan described in Table 1 in Xu et al., "Kinetics of acid hydrolysis of water-soluble spruce O-acetyl galactoglucomannans," *Journal of agricultural and food chemistry* 56 7 (2008): 2429-2435, which is hereby incorporated by reference herein.

Example 7

Process Demonstration with Multiple Pressure Cycles 180 mM sulfuric acid is infused into softwood chips and the amount of free sugars produced when not using pressure cycling is compared with that using pressure cycling. In this experiment, two infusion vessels are used: one without pressure cycling, and another with pressure cycling. Into each infusion vessel, 400 mL of water with 180 mM sulfuric acid is infused at 16 kPa into 50 g of 12 mm softwood cubes. The water is infused at 50° C. After infusion, the pressure is restored to 100 kPa and the operating temperature is raised to 90° C.

Samples are taken from each vessel every 30 minutes for 7 hours. In one of the vessels, immediately prior to taking the sample, the pressure is reduced to about 70 kPa for 5 minutes so that the water boils; then the pressure is rapidly restored to 100 kPa. Samples are taken at the same time from each infusion vessel. Table 5 shows the amount of free sugar in the liquid (g/L) in the two infusion vessels.

The results shown in Table 5 indicate a faster rise in free sugar when the pressure is cycled. The improved mass transfer afforded by the periodical mixing of the liquid through the rapid pressure changes and induced bubble formation contribute to both increase the hydrolysis rate and in removing free sugars from the wood fiber lumen into the bulk liquid. This demonstrates that pressure cycling dramatically improves the performance of vacuum infusion by overcoming diffusion limitations without the need of any additional mechanical mixing.

TABLE 5

Sugar Concentrations (g/L) without and with Pressure Cycling (Example 7)

| Time (hr) | Static | Cycled |
|---|---|---|
| 0.0 | 0 | 0 |
| 0.5 | 2 | 2 |
| 1.0 | 3 | 4 |
| 1.5 | 4 | 7 |
| 2.0 | 5 | 8 |
| 2.5 | 6 | 10 |
| 3.0 | 7 | 13 |
| 3.5 | 6 | 13 |
| 4.0 | 7 | 15 |
| 4.5 | 9 | 19 |
| 5.0 | 10 | 24 |
| 5.5 | 10 | 27 |
| 6.0 | 11 | 31 |
| 6.5 | 11 | 33 |
| 7.0 | 12 | 35 |

In this detailed description, reference has been made to multiple embodiments and to the accompanying drawings in which are shown by way of illustration specific exemplary embodiments of the invention. These embodiments are described to enable those skilled in the art to practice the invention, and it is to be understood that modifications to the various disclosed embodiments may be made by a skilled artisan.

Where methods and steps described above indicate certain events occurring in certain order, those of ordinary skill in the art will recognize that the ordering of certain steps may be modified and that such modifications are in accordance with the variations of the invention. Additionally, certain steps may be performed concurrently in a parallel process when possible, as well as performed sequentially.

All publications, patents, and patent applications cited in this specification are herein incorporated by reference in their entirety as if each publication, patent, or patent application were specifically and individually put forth herein.

The embodiments, variations, and FIGURES described above should provide an indication of the utility and versatility of the present invention. Other embodiments that do not provide all of the features and advantages set forth herein may also be utilized, without departing from the spirit and scope of the present invention. Such modifications and variations are considered to be within the scope of the invention defined by the claims. In the case of conflict in definitions between the present disclosure and a dictionary or other reference, the present disclosure will be controlling.

What is claimed is:

1. A process for producing sugar monomers and/or polymers from a carbohydrate-rich substrate, said process comprising the steps of:
   (a) providing a carbohydrate-rich substrate and an aqueous solution containing a hydrolysis catalyst, and maintaining a gas pressure above said carbohydrate-rich substrate at an evacuation pressure and for an evacuation time to infuse said hydrolysis catalyst into said carbohydrate-rich substrate at an infusion temperature, thereby generating a reaction mixture;
   (b) exposing said reaction mixture to a gas-phase reaction pressure that is higher than said evacuation pressure;
   (c) maintaining said reaction mixture at a reaction temperature for a reaction time to generate said sugar monomers and/or polymers within lumen space of said carbohydrate-rich substrate;
   (d) exposing said reaction mixture to a gas-phase expulsion pressure that is lower than said reaction pressure, to pump said sugar monomers and/or polymers out of said lumen space and into said aqueous solution;
   (e) maintaining said reaction mixture at an expulsion temperature for an expulsion time;
   (f) repeating steps (b) to (e) for at least two pressure cycles to remove, by a pumping mechanism, said sugar monomers and/or polymers from said lumen space; and
   (g) recovering said sugar monomers and/or polymers from said aqueous solution;
   wherein said process does not include steam explosion or ammonia fiber expansion of said carbohydrate-rich substrate.

2. The process of claim 1, wherein said carbohydrate-rich substrate is selected from the group consisting of naturally occurring lignocellulosic biomass, processed lignocellulosic biomass, pulp, paper, paper-based products, carbohydrate-rich industrial waste, and combinations thereof.

3. The process of claim 2, wherein said carbohydrate-rich substrate includes said naturally occurring lignocellulosic biomass selected from the group consisting of size-reduced softwood, sugarcane bagasse, wheat straw, corn stover, switchgrass, miscanthus, and combinations thereof.

4. The process of claim 2, wherein said carbohydrate-rich substrate includes carbohydrate-rich industrial waste selected from the group consisting of food waste, components of municipal solid waste, and combinations thereof.

5. The process of claim 1, wherein said sugar monomers and/or polymers comprise pentose and/or hexose sugars in monomer, oligomer, or polymer form, including one or more of xylose, arabinose, glucose, mannose, galactose, O-acetyl galactoglucomannan, and nanocellulose crystals.

6. The process of claim 1, wherein said hydrolysis catalyst comprises an organic acid, a mineral acid, hydrogen peroxide, or a combination thereof.

7. The process of claim 6, wherein said hydrolysis catalyst comprises sulfuric acid in an amount that results in said aqueous solution having a sulfuric acid concentration of about 10 mM to about 200 mM.

8. The process of claim 1, wherein said hydrolysis catalyst comprises one or more Fenton or Fenton-like reagents including hydrogen peroxide and one or multiple transition metals forming a molar ratio of said hydrogen peroxide to said transition metals of about 20 to about 100.

9. The process of claim 1, wherein said hydrolysis catalyst comprises one or more enzymes each with cellulolytic activity and/or hemicellulolytic activity.

10. The process of claim 1, wherein said aqueous solution in step (a) is a homogeneous mixture, said process further comprising mixing said hydrolysis catalyst with process water using turbulent energy in the range of about 0.5 W/kg to about 5 W/kg to produce said homogeneous mixture.

11. The process of claim 1, wherein said reaction temperature is about 40° C. to about 95° C. and/or said reaction time is about 15 minutes to about 8 hours.

12. The process of claim 1, wherein said expulsion time is about 1 second to about 60 minutes.

13. The process of claim 1, wherein said expulsion pressure is from about 100% to about 200% of the water equilibrium pressure at said reaction temperature.

14. The process of claim 1, wherein said number of pressure cycles is from 3 to about 200.

15. The process of claim 1, wherein said infusion temperature is less than or equal to the boiling point of water at said evacuation pressure.

16. The process of claim 1, wherein said infusion temperature is from about 40° C. to about 90° C.

17. The process of claim 1, wherein said evacuation pressure is from about 105% to about 200% of the water equilibrium pressure at said infusion temperature.

18. The process of claim 1, wherein said evacuation time is about 1 minute to about 2 hours.

19. The process of claim 1, said process further comprising controlling pH of said reaction mixture by adjusting gas-phase composition above, or in equilibrium with, said aqueous solution.

20. The process of claim 19, wherein said hydrolysis catalyst comprises an organic acid, a mineral acid, or a combination thereof, and wherein said pH is controlled to about 2 or less.

21. The process of claim 19, wherein said hydrolysis catalyst comprises one or more Fenton or Fenton-like reagents and optionally one or more mineral acids, and wherein said pH is controlled between about 1 to about 6.

22. The process of claim 19, wherein said hydrolysis catalyst comprises one or more enzymes each with cellulolytic activity and/or hemicellulolytic activity, and wherein said pH is controlled between about 4 to about 7.

23. A method of producing sugar monomers and/or polymers from a carbohydrate-rich substrate having lumen space, said method comprising hydrolyzing said carbohydrate-rich substrate in the presence of an aqueous solution containing a hydrolysis catalyst, and cycling gas pressure between a reaction pressure and an expulsion pressure for at least three pressure cycles, wherein at said reaction pressure, said sugar monomers and/or polymers are generated within said lumen space, and wherein at said expulsion pressure, said sugar monomers and/or polymers are pumped out of said lumen space and into said aqueous solution, wherein said method does not include steam explosion or ammonia fiber expansion of said carbohydrate-rich substrate.

24. The method of claim 23, wherein the mass-transfer rate of said sugar monomers and/or polymers transporting out of said lumen space is higher than the diffusion rate of said sugar monomers and/or polymers diffusing out of said lumen space.

25. The method of claim 23, wherein reaction rate of generation of said sugar monomers and/or polymers is higher than an otherwise-identical process without a step of cycling said gas pressure.

\* \* \* \* \*